United States Patent
Boyce et al.

(10) Patent No.: US 6,332,779 B1
(45) Date of Patent: Dec. 25, 2001

(54) METHOD OF HARD TISSUE REPAIR

(75) Inventors: Todd M. Boyce, Aberdeen; David Kaes, Toms River; Nelson L. Scarborough, Ocean; Samantha Salkeld, Cliffwood, all of NJ (US)

(73) Assignee: Osteotech, Inc., Eatontown, NJ (US)

( * ) Notice: Subject to any disclaimer, the term of this patent is extended or adjusted under 35 U.S.C. 154(b) by 25 days.

(21) Appl. No.: 09/609,982

(22) Filed: Jul. 3, 2000

(51) Int. Cl.$^7$ ........................................... A61C 5/00
(52) U.S. Cl. .................. 433/215; 623/11.11; 623/13.11; 623/16.11
(58) Field of Search ............... 623/11.11, 16.11, 623/13.11, 13.17; 523/113, 115; 433/215

(56) References Cited

U.S. PATENT DOCUMENTS

| | | |
|---|---|---|
| 4,394,370 | 7/1983 | Jefferies . |
| 4,678,470 | 7/1987 | Nashef et al. . |
| 4,743,259 | 5/1988 | Bolander et al. . |
| 4,902,296 | 2/1990 | Bolander et al. . |
| 4,932,973 | 6/1990 | Gendler . |
| 5,032,445 | 7/1991 | Scantlebury et al. . |
| 5,073,373 | 12/1991 | O'Leary et al. . |
| 5,464,439 | 11/1995 | Gendler . |
| 5,507,813 | 4/1996 | Dowd et al. . |
| 5,556,430 | 9/1996 | Gendler . |
| 5,607,269 | 3/1997 | Dowd et al. . |
| 5,641,518 | 6/1997 | Badylak et al. . |
| 5,683,459 | 11/1997 | Brekke . |
| 5,700,479 | 12/1997 | Lundgren . |
| 5,899,939 | 5/1999 | Boyce et al. . |
| 6,162,258 * | 12/2000 | Scarborough et al. ........... 623/23.63 |
| 6,294,041 * | 9/2001 | Boyce et al. ....................... 156/275.5 |
| 6,294,187 * | 9/2001 | Boyce et al. ......................... 424/422 |

* cited by examiner

Primary Examiner—Nicholas D. Lucchesi
(74) Attorney, Agent, or Firm—Dilworth & Barrese, LLP

(57) ABSTRACT

A method for promoting the growth of bone, periodontium, or ligament in a warm-blooded vertebrate, the method comprising: producing a surgical flap to expose the bone, periodontium or ligament; debriding the bone, periodontium or ligament to remove organic matter from the bone, periodontium or ligament; implanting an effective amount of an osteogenic bone graft material, the bone graft material consisting of an osteoimplant having not greater than about 32% void volume formed at least in part from elongate bone-derived elements optionally in combination with bone powder; replacing the flap; and, allowing the bone, periodontium or ligament to regrow.

10 Claims, No Drawings

METHOD OF HARD TISSUE REPAIR

BACKGROUND OF THE INVENTION

This invention relates to an osteogenic osteoimplant made up of, at least in part, elongate bone-derived elements for use in the repair, replacement and/or augmentation of various portions of animal or human skeletal systems. More particularly, this invention relates to the use of an implant made up of a coherent mass of elongate bone-derived elements optionally in combination with bone powder. The elongate bone-derived elements and/or bone powder may be undemineralized bone, partially or fully demineralized bone, or any combination thereof. The method of the invention herein is especially useful in periodontal applications, e.g., guided bone regeneration; plastic and reconstructive surgery, e.g., where the contour of the bone must be modified; and filling of cranial defects; though other skeletal applications are also envisioned.

The use of pulverized exogenous bone growth material, e.g., derived from demineralized allogenic or xenogenic bone, in the surgical repair or reconstruction of defective or diseased bone is known. See, in this regard, the disclosures of U.S. Pat. Nos. 4,394,370, 4,440,750, 4,472,840, 4,485,097, 4,678,470, and 4,743,259; Bolander et al., "The Use of Demineralized Bone Matrix in the Repair of Segmental Defects", *The Journal of Bone and Joint Surgery*, Vol. 68-A, No. 8, pp. 1264–1273; Glowacki et al, "Demineralized Bone Implants", *Symposium on Horizons in Plastic Surgery*, Vol. 12, No. 2; pp. 233–241 (1985); Gepstein et al., "Bridging Large Defects in Bone by Demineralized Bone Matrix in the Form of a Powder", *The Journal of Bone and Joint Surgery*, Vol. 69-A, No. 7, pp. 984–991 (1987); Mellonig, "Decalcified Freeze-Dried Bone Allograft as an Implant Material In Human Periodontal Defects", *The International Journal of Periodontics and Restorative Dentistry*, pp. 41–45 (June, 1984); Kaban et al., "Treatment of Jaw Defects with Demineralized Bone Implants", *Journal of Oral and Maxillofacial Surgery*, pp.623–626 (Jun. 6, 1989); and, Todescan et al., "A Small Animal Model for Investigating Endosseous Dental Implants: Effect of Graft Materials on Healing of Endosseous, Porous-Surfaced Implants Placed in a Fresh Extraction Socket", *The International Journal of Oral & Maxillofacial Implants* Vol. 2, No. 4, pp. 217–223 (1987).

More recently, processed bone has been developed into new shapes for use in new surgical applications, or as new materials for implants that were historically made of non-biologically derived materials.

U.S. Pat. No. 5,556,430 describes the use of a continuous sheet of demineralized bone or partially demineralized bone, however, the sheet must be sufficiently flexible, therefore sacrificing strength, in order to conform to the skeletal site to which it is applied.

However, the prior art demineralized bone products have proven to be unsatisfactory for applications requiring a thin osteogenic material capable of displaying a variety of properties. Commonly assigned U.S. application Ser. No. 09/610,026 filed on even date herewith and incorporated herein by reference discloses a new osteogenic implant.

In one embodiment, the material is thin and conforming, i.e., able to be shaped closely to the exterior of bony surfaces, thereby minimizing stress on the overlying soft tissues. In a different embodiment, the material is form holding, i.e., able to maintain its three-dimensional architecture even after rehydration and deformation prior to or during implantation. This new thin osteogenic material capable of displaying a variety of properties is useful in surgical applications that previously were difficult to successfully treat, e.g., periodontal defects.

BACKGROUND OF THE INVENTION

Membrane barrier devices are used as physical barriers to epithelial cell migration in the treatment of periodontal defects through the principles of guided tissue regeneration (GTR). The concept of guided tissue regeneration was developed by Nyman, S. et al. "New attachment formation by guided tissue regeneration." *J. Perio. Res.*, 1987, 22(3) 252–254 and in practice involves the use of a biocompatible material capable of separating two cell populations in vivo. The principle is as follows: When an empty space is created in a living tissue, it is filled by the most rapidly multiplying cell line adjacent to this void, unless access is deliberately limited to a single cell type, which will then be the only one to colonize the void to be filled. The principle is utilized in guided tissue regeneration for directing the repair of damaged tissues in the manner desired by the clinician. Thus, for example, in the case of periodontology, it is very difficult to repair damaged periradicular ligamentaous tissue. In fact, during the periodontium healing process, the epithelium regenerates more rapidly than the ligament and tends to take its place. The guided tissue regeneration technique used in this case consists in isolating the region normally occupied by the ligament, so as to make it inaccessible to the epithelium. This operation can be performed with a biocompatible material implanted in the tissues.

The materials currently in clinical use, with a few notable exceptions, e.g., titanium-reinforced membrane and calcium sulfate (Capset), are non-rigid, non-space maintaining, and do not possess osteoinductive properties. Such currently available materials, e.g., resorbable barrier membranes, are typically fabricated from collagen or polymers and are generally understood to be inferior to the non-resorbable materials due to premature degradation of the barrier properties. The notable exceptions, titanium-reinforced membrane and calcium sulfate (Capset), are not without their limitations.

Although titanium serves to add rigidity and volume beneath the membrane, this material must be removed and is technically demanding to implant and maintain. Calcium sulfate, when placed atop a bone graft material during operative repair of a periodontal lesion, sets up (hardens) intraoperatively and is resorbable. However, calcium sulfate does not posses osteoinductive properties and its efficacy, as a barrier to epithelial migration or oral contaminants, is uncharacterized. U.S. Pat. No. 5,700,479 describes an element and method for selective regeneration of any tissues in a living human or animal body tissues subjected to healing. U.S. Pat. No. 5,032,445 describes the use of a biocompatible porous material, such as expanded polytetrafluoroethylene (PTFE), for separating the gingival tissue from the tooth surface in an area where periodontal disease is present, or for treatment of bony defects. Therefore one object of this invention is to provide a method of using an osteogenic barrier membrane which possesses physical membrane attributes while avoiding reoperative removal procedures.

In addition to the periodontal application, any bone or bone area throughout the whole body available for surgical intervention can be treated by using the method of the present invention. The aim of the treatment might be a predictable filling out of bone defects of different sizes and shapes in the edentulous jaw bone or adjacent to teeth or bone-anchored implants, as well as, bone defects anywhere else within the body such as in the maxillofacial bones, in the skull bones, in the long bones, in the hand and foot bones, and in the back bones. The defects might have well-defined borderlines or successively pass into the surrounding bones and their bottom and wall surfaces can contain more or less of compact (cortical) bone. The defects might be so narrow as to be defined as bone depressions rather than bone defects. In fact, there are many sites where the bone surface to be chosen for regeneration is flat or convex rather than concave, but where there are strong indications for building up rather than filling out bone. The bone defect can also include a fracture optionally in combination with skull bone and/or jaw bone defects. The method of the present invention may also be used in situations where there are indications for elongation (or shortening) of bones, for instance, of jaw bones and long bones. The technique can be used to collect bone for transplantation.

There are many causes of the above-described bone defects, such as congenital defects, traumatic lesions, defects caused by tooth extractions, surgically induced defects, osteitis, cysts, tumors, periodontal destructions, bone resorptions due to overloading, infections or internal diseases. These defects may be functional and/or aesthetic in nature. Other therapeutic measures might be based solely on aesthetic indications for correction of deformities or aesthetic "improvements" of the appearance. Many of the mentioned indications will be elucidated and described in detail below in conjunction with the different embodiments and exemplifications. Thus, a second object of the invention is to provide a method of treating bone defects that requires a thin osteogenic membrane like material.

SUMMARY OF THE INVENTION

In keeping with these and related objects of the invention, there is provided a method for promoting the growth of bone, periodontium, or ligament in a warm-blooded vertebrate, the method comprising: producing a surgical flap to expose the bone, periodontium or ligament; debriding the bone, periodontium or ligament to remove organic matter from the bone, periodontium or ligament; implanting an effective amount of an osteogenic bone graft material, the bone graft material consisting of an osteoimplant having not greater than about 32% void volume formed, at least in part, from elongate bone-derived elements optionally in combination with bone powder; replacing the flap; and, allowing the bone, periodontium or ligament to regrow.

There is also provided a method of providing selective influence on tissue regeneration in the vicinity of a periodontal defect, said method comprising the steps of (a) separating soft tissue from at least a portion of the surface of a root of a tooth located at the defect, the portion comprising that area of the root surface located adjacent to the defect;

(b) affixing to the root surface an osteoimplant having not greater than about 32% void volume formed, at least in part, from elongate bone-derived elements optionally in combination with bone powder and having one surface that is impermeable to soft-tissue cells;

(c) tightly affixing the osteoimplant near or slightly apical to the cervix of the root to prevent the growth in an apical direction of soft tissue along the root surface; and (d) closing the soft tissue over the osteoimplant.

Such a method would be useful in the treatment of periodontal defects, i.e., any bony defect that arises from periodontal disease in which resolution of the defect would preserve and maintain a tooth or teeth. Periodontal defects to be treated with the demineralized bone material include but are not limited to Class I through III, where class III is further distinguished into subclasses A and B, e.g., infra and intra bony defects, defects of either or both the lingual and buccal alveolar ridge and defects of the alveolar ridge involving either or both the ridge height and width.

The number of walls a defect has and if the walls are bone are used to describe a periodontal defect in addition to the Classes I through III. The architecture of a challenging periodontal defect is such that few of the defect walls are bone. The more bony walls a defect has the greater the probability for bone regeneration following a periodontal treatment. At least one wall of the defect is bound by a tooth root which can not participate in periodontal regeneration or bone healing. Another wall can be gingival tissue which, if uncontained, will proliferate to fill in the defect before bone can form. A barrier serves to exclude the epithelial cells that come from the gingival tissue wall. A conventional barrier material, in the absence of bony walls around a periodontal defect and the affected tooth, makes it difficult to maintain space and regrow bone height toward the cemento-enamel junction.

The method of the invention is also useful in procedures such as ridge augmentation and other oral maxillofacial reconstructive procedures. Such procedures would include but not be limited to, e.g., the repair of extraction socket defects, residual defects from the loss or removal of a tooth or teeth, defects resulting from the resorption of bone that supports or supported a tooth root, long term edentulous regions, sites that require additional bony support for the placement of dental implant, in the buccal, lingual, mesial, or distal directions, bone grafting for the same in either the mandible or maxilla, defects arising from the harvest of bone graft from any number of sites including the symphysis, the ramus, or the posterior mandible.

The method of the invention is also useful in the treatment of craniofacial deformities including but not limited to traumatic bone loss, fractures, defects from nonunion of craniofacial fractures or injuries, defects arising from craniotomy or osteotomy, residual defects as a result of craniotomy or osteotomy, congenital deformities or defects resulting from the surgical correction of congenital deformities.

The method of the invention is also useful in the treatment of bone defects in other areas, such as general orthopedics, wrapping fractures, wrapping osteogenic materials to maintain placement, etc.

The term "osteoimplant" as used herein refers to a bone-derived implant having not greater than about 32% average void volume formed, at least in part, from elongate bone-derived elements optionally in combination with bone powder and therefore is intended to include expressions such as bone membrane, bone graft, etc.

The expression "void volume" as used herein shall be understood to refer to the average amount of non-solid space contained within the implant of this invention. Such space will be considered to be void volume even if it contains a substance that is liquid at ambient temperature, e.g., between 0.5° and 50° C.

The term "osteogenic" as applied to the osteoimplant of this invention shall be understood as referring to the ability of the osteoimplant to enhance or accelerate the in growth of new bone tissue by one or more mechanisms such as osteogenesis, osteoconduction and or osteoinduction.

The term "osteoinductive" as used herein shall be understood to refer to the ability of a substance to recruit cells from the host which have the potential for repairing bone tissue.

The term "osteoconductive" as used herein shall be understood to refer to the ability of a substance to provide biologically inert surfaces which are receptive to the growth of new host bone.

The expression "guided bone regeneration" (GBR) or "guided tissue regeneration" (GTR) as applied to this invention refers to the ability to induce sufficient bone growth before competitive, faster-growing tissue and epithelial cells fill the bone repair site.

The terms "impermeable" and "occlusive" are utilized herein interchangeably and shall be understood as referring to any zone, i.e., surface area, of the osteoimplant of this invention which possesses an average pore size which substantially prevents the ingrowth of soft tissue, i.e., an average pore size of from about 3 to about 500 microns.

The term "integral" as used herein is intended to differentiate the osteoimplant useful in the method of this invention from osteoimplants which are combined with a separate barrier membrane material. In the instant invention, the osteoimplant and zone of impermeability are integral with one another, i.e., they are indivisibly interconnected so as to form a single, unified whole.

Use of the expression "bone-derived elements" and expressions of like import shall be understood to refer to pieces of bone in any variety of sizes, thicknesses and configurations including particles, fibers, strips, etc., which can be obtained by milling, shaving, cutting or machining whole bone with the proviso that such elements are not envisioned as containing layers as set forth in U.S. Pat. No. 5,899,939.

The term "demineralized" as used herein refers to bone containing less than its original mineral content and is intended to encompass such expressions as "substantially demineralized", "partially demineralized" and "fully demineralized".

As utilized herein, the expression "superficially demineralized" refers to bone-derived elements possessing at least about 90 weight percent of their original inorganic mineral content, the expression "partially demineralized" refers to bone-derived elements possessing from about 8 to about 90 weight percent of their original inorganic mineral content and the expression "fully demineralized" refers to bone containing less than 8% of its original mineral context.

The term "occluding" as utilized herein shall be understood to refer to any operation or process which reduces the porosity of a region of the ostegenic osteoimplant thus rendering such surface area substantially impermeable to the ingrowth of soft tissue, i.e., undesired cells and soft tissues that are competitive to bone formation.

DETAILED DESCRIPTION OF THE INVENTION

The osteogenic osteoimplant useful in the present invention comprises an aggregate of bone-derived particles and, optionally, biocompatible substances, having not greater than about 32% void volume.

To fabricate the osteoimplant useful in the practice of this invention, a coherent mass of bone-derived particles is first produced followed by mechanically shaping the mass to form the osteogenic osteoimplant. The osteoimplant useful herein can have a wide variety of properties and characteristics depending upon the ratio of elongate bone particles to bone powder, the degree of demineralization of these bone-derived elements, and the presence of optional biocompatible substances. Of course it will be recognized by one skilled in the art to which this invention most closely pertains that the selective addition of bio-compatible substances as well as any additional treatment(s) of the osteoimplant useful herein before, during, or after processing or, optionally, after processing but before or during implantation will also affect the properties and characteristics of the osteoimplant. Such routine variation is envisioned as being within the scope of this invention as detailed in the specification and examples herein.

In a preferred embodiment of the invention, the bone elements that comprise the osteoimplant are fully demineralized prior to being mechanically shaped into the osteoimplant of the invention. Thereafter, a portion of the surface area of the osteoimplant is optionally occluded to reduce the porosity of the surface area so as to render that surface area impermeable to the ingrowth of soft tissue.

The osteoimplant can be optionally pre-shaped to a specific shape and/or contour. The resulting osteoimplant can assume a determined or regular form or configuration such as a sheet, plate, disk, tunnel, cone, tube, to name but a few. Prefabricated geometry would include, but not be limited to, a crescent apron for single site use, an I-shape to be placed between teeth for intra bony defects, a rectangular bib for defects involving both the buccal and lingual alveolar ridges, neutralization plates, reconstructive plates, buttress plates, T buttress plates, spoon plates, clover leaf plates, condylar plates, compression plates, bridge plates, wave plates, etc. Partial tubular as well as flat plates can be fabricated from the osteoimplant of this invention. Of course, the osteoimplant can be machined or shaped by any suitable mechanical shaping means. Computerized modeling can, for example, be employed to provide an intricately-shaped osteoimplant which is custom-fitted to the bone repair site with great precision.

The osteoimplant useful in the method of the invention herein is intended to be applied at a bone repair site, e.g., one resulting from injury, defect brought about during the course of surgery, infection, malignancy or developmental malformation. The osteoimplant can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filing, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, inlay osteoimplants, implant placement and revision, sinus lifts, cosmetic enhancement, etc. Specific bones which can be repaired or replaced with the osteoimplant utilizing the method herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

At the bone repair site, the osteoimplant can be employed in the dry or hydrated state. The dry or hydrated osteoimplant can be cut or sized if need be to conform to the site being repaired. The osteoimplant can be implanted at the bone repair site, if desired, using any suitable affixation means, e.g., sutures, staples, bioadhesives, and the like or may be laid in position and affixed by the soft tissue surgically closed over it.

When the osteoimplant has barrier membrane properties, the method of this invention finds particular utility in the field of periodontal surgery such as alveolar ridge augmentation. The osteoimplant is applied to a periodontal repair site, e.g., one walled defect bound by the tooth root, with the implant extending from the cemento-enamel junction to beyond the distal extent of the defect in such a manner that the zone of impermeability to soft tissue ingrowth lies above the bone line where soft tissue resides and the untreated portion of the osteoimplant is in contact with bone tissue. In this manner, soft tissue ingrowth above the bone line is prevented or abated, thus obviating the need for a separate guided bone regeneration (GBR) membrane and allowing for the slower growing bone tissue to populate the region lying below the bone line. This results in a more efficient, simpler surgical procedure, eliminates the cost of a separate GBR membrane and its implantation drawbacks and reduces the likelihood of infection (as the native collagen of the bone particles does not have the same tendency as synthetic implants to act as a nidus for infection). Also, use of the osteoimplant to treat such conditions provides the osteoinductive factors of the osteoimplant where most needed to enhance bone regeneration over soft tissue migration.

When the osteoimplant is in the form of partially demineralized plates, possible clinical applications include the treatment of traumatic fractures, pathologic fractures, stress fractures, congenital defects or fractures, or operative defects in any bone of the body. Fracture categories can include but are not limited to intraarticular or periarticular fractures, metaphyseal fractures, transverse, oblique, comminuted, and fragmented fractures.

When the osteoimplant is in the form of a conformable sheet, it can be wrapped around surgical sites where other osteogenic material, e.g., allograft and/or autograft, has been placed to aid in maintaining the retention of the other osteogenic material where it has been placed by the surgeon. Optionally, the conformable sheet can be used to create a package of osteogenic material, e.g., allograft and/or autograft, that will remain where placed by the surgeon even when the surgical site is subjected to repeated irrigation.

USE OF THE OSTEOGENIC OSTEOIMPLANT

The osteogenic osteoimplant useful herein is intended to be applied at a bone repair site, e.g., one resulting from injury, defect brought about during the course of surgery, infection, malignancy or developmental malformation. The method herein can be utilized in a wide variety of orthopedic, periodontal, neurosurgical and oral and maxillofacial surgical procedures such as the repair of simple and compound fractures and non-unions; external and internal fixations; joint reconstructions such as arthrodesis; general ardiroplasty; cup arthroplasty of the hip; femoral and humeral head replacement; femoral head surface replacement and total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic procedures; etc. Specific bones which can be repaired or replaced utilizing the method herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

Possible clinical applications would include, e.g., the treatment of traumatic fractures, pathologic fractures, stress fractures, congenital defects or fractures, or operative defects in any bone of the body that would be treated with plate fixation. Fracture categories treated with the osteoimplant can include but not be limited to intraarticular or periarticular fractures; metaphyseal fractures; transverse, oblique, comminuted, and fragmented fractures; repair to non-fractured sites; defects due to periodontal disease or surgery; and other bone defects.

At the bone repair site, the osteogenic osteoimplant can be employed in the dry or hydrated state. The dry or hydrated osteoimplant can be cut or sized if need be to conform to the site being repaired. The osteoimplant can be hydrated before, during or after implantation with a suitable biocompatible liquid, e.g., water, saline solution, etc., for a period of time ranging from about 1 to about 120 minutes depending on the thickness of the osteoimplant. The osteoimplant can be packaged in either the dried or wet state and stored for subsequent application. In some circumstances, it is preferable to package the osteoimplant in the wet state so that it is ready for immediate use at the surgical site. After being hydrated, a preferred embodiment of the osteoimplant becomes flexible yet retains its shape and much of its tensile strength.

Optional materials can also be added to the osteoimplant prior to or after its placement at the surgical site. For example, at the time just prior to when the osteoimplant of the invention is to be placed in a defect site optional materials, e.g., autograft bone marrow aspirate, autograft bone, preparations of selected autograft cells, autograft cells containing genes encoding bone promoting action, any other agent which induces or accelerates appropriate healing, etc., can be combined with the osteoimplant of this invention.

The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

The invention will be more fully understood by way of the following examples which are intended to illustrate but not limit methods of preparation of the osteogenic osteoimplant in accordance with the present invention.

EXAMPLE 1

PERIODONTAL DEFECTS

An incision is made through the muco-gingival tissue in the involved defect region and a muco-periosteal flap is raised away from the crest of the supporting bone. After careful debridement of any granulation or infected tissue, root scaling is performed with curetts. At this point, treatment to the effected tooth is performed. This treatment can include the application of an antimicrobial agent such as antibiotic or treatment of the root with a decalcifying agent or both according to standard techniques. In addition, bone grafting may be performed with autogenous bone locally obtained or otherwise, bone graft substitutes such as ceramic particles, or with demineralized bone matrix. After the graft is placed, the demineralized bone membrane is cut to a shape by the surgeon such that it completely covers the graft site or the non-grafted site, if applicable. The demineralized bone membrane is formed by hand to the natural contour of the original alveolar ridge, thus providing space for the regeneration of new bone. When the demineralized bone membrane has barrier membrane properties, it is placed in such a manner that the zone of impermeability to soft tissue ingrowth lies above the bone line where soft tissue resides and the untreated portion of the osteoimplant is in contact with bone tissue. In this manner, soft tissue ingrowth above the bone line is prevented or abated, thus obviating the need for a separate guided bone regeneration (GBR) membrane and allowing for the slower growing bone tissue to populate the region lying below the bone line. The soft tissue flaps are then re-approximated over the dimineralized bone membrane with tension free resorbable suture. The same procedure can be followed with or without root conditioning treatments or with or without bone grafting procedures.

EXAMPLE 2

CRANIOFACIAL DEFORMITIES

After obtaining exposure of the region of the defect, the site is debrided, if necessary, until any granulation, infected, avascular or undesirable soft tissues are removed and punctate bleeding is observed. The defect may require stabilization, alignment, or reduction through the use of plates, screws, internal or external fixation device prior to grafting. The defect is grafted with an appropriate bone graft material to restore the contours of the defect. The partially demineralized osteoimplant is trimmed such that the resulting piece completely covers the graft material and the borders of the supporting host bone. The osteoimplant is held in place with resorbable suture by anchoring the osteoimplant to the periosteum, if available. Alternatively the osteoimplant is held in place by bone screws, staples, resorbable anchors, or other fixative device. In a defect that is not subject to loading, fixing the osteoimplant may not be necessary. After complete coverage of the site is achieved, soft tissues are re-approximated by standard surgical techniques.

EXAMPLE 3

RIDGE AUGMENTATION AND OTHER ORAL MAIXLLOFACIAL RECONSTRUCTIVE PROCEDURES

After obtaining exposure of the region of the defect, the site is debrided, if necessary, until punctuate bleedings is observed. The defect is grafted with an appropriate bone graft material to restore the contours of the defect or build sufficient ridge width and height to accommodate endosseous implants. The demineralized bone membrane is trimmed such that the resulting piece completely covers the graft material and the borders of the supporting host bone. The demineralized bone membrane is held in place with resorbable suture by anchoring the bone membrane to the periosteum of the supporting host bone, if available. Alternatively the demineralized bone membrane can be held in place by bone screws, staples, resorbable anchors, or other fixative device. In a defect that is not subject to loading, fixing the bone membrane may not be necessary. After complete coverage of the site is achieved, the soft tissues are re-approximated by standard surgical techniques.

EXAMPLE 4

USE OF RESORBABLE PLATES

After obtaining surgical exposure of the fracture or osseous defect site, the fragments, if present, are aligned anatomically with standard reduction instruments and procedures. A partially demineralized osteoimplant of the appropriate size, length, and width is chosen based on the available area for fixation and the biomechanical principles of the osteoimplant. The osteoimplant is bent by hand or with an instrument designed for the purpose to conform to the desire; contours. Drill holes are made with the use of the osteoimplant or a template as a guide. Screws, e.g., lag, compression, resorbable or nonresorbable, are then placed through the osteoimplant or through predrilled holes in the osteoimplant, such that a load is placed across the defect bringing the fragments in contact. With the partially demineralized osteoimplant in position, the screws are inserted and tightened. Closure is obtained with standard techniques.

EXAMPLE 5

USE OF DEMINERALIZED SHEET

After obtaining surgical exposure of the fracture or osseous defect site, the fragments, if present, are aligned anatomically with standard reduction instruments and procedures. Bone graft materials are then placed at the site. A fully demineralized osteoimplant which optionally contains biocompatible fluid carrier of the appropriate size, length and width is chosen based on the available volume of the surgical site and is wrapped around the site to hold the graft material in place at the site the surgeon places it. The fully demineralized osteoimplant is retained in position using standard methods. Closure is obtained with standard techniques.

EXAMPLE 6

SPINAL FUSION

After obtaining exposure of the implant site, e.g. lumbar vertebrae $L_4$ through $L_6$, the cortex of the transverse and/or articular processes is removed to expose the cancellous bone beneath. Osteogenic material, autograft and/or allograft, is placed on top of a fully demineralized osteoimplant which opionally contains biocompatible fluid carrier of the appropriate size, length and width based on the volume of osteogenic material and the dimension of the implant site. The osteoimplant is folded around the osteogenic material to form an envelope containing the osteogenic material which is then placed at the implant site. The envelope containing osteogenic material is retained using standard methods. Closure is obtained with standard techniques.

What is claimed is:

1. A method for promoting the growth of bone, periodontium, or ligament in a warm-blooded vertebrate, he method comprising:

producing a surgical flap to expose the bone, periodontium or ligament;

debriding the bone, periodontium or ligament to remove organic matter from the bone, periodontium or ligament;

implanting an effective amount of an osteogenic bone graft material, the bone graft material consisting of an osteoimplant having not greater than about 32% void volume formed, at least in part, from elongate bone-derived elements optionally in combination with bone powder;

replacing the flap; and, allowing the bone, periodontium or ligament to regrow.

2. The method of claim 1 wherein the bone graft material is formed into a predetermined shape.

3. The method of claim 2 wherein the predetermined shape is a 3-dimensional shape.

4. The method of claim 1 wherein the bone graft material is partially demineralized.

5. The method of claim 1 wherein the bone graft material is fully demineralized.

6. The method of claim 1 wherein one surface of the bone graft material is less permeable to cells.

7. The method of claim 1 wherein the osteoimplant further comprises an optional material selected from the group consisting of autograft bone marrow aspirate, autograft bone, preparations of selectee autograft, and autograft cells containing genes encoding bone promoting action and mixtures thereof.

8. The method of claim 1 wherein the osteoimplant further comprises a biocompatible component selected from the group consisting of biocompatible fluid carrier, biocompatible binder, filler, fiber, mesh, substance providing radiopacity, plasticizer, biostatic/biocidal agent, surface active agent, bioactive substance and mixtures thereof.

9. The method of claim 1 further comprising placing osteogenic material on the osteoimplant and folding the osteoimplant to contain the osteogenic material.

10. A method of providing selective influence on tissue regeneration in the vicinity of a periodontal defect, said method comprising the steps of separating soft tissue from at least a portion of the surface of a root of a tooth located at the defect, the portion comprising that area of the root surface located adjacent to the defect; and affixing to the root surface an osteoimplant having not greater than about 32% void volume formed at least in part from elongate bone-derived elements optionally in combination with bone powder and having one surface that is impermeable to soft-tissue cells; and, tightly affixing the osteoimplant near or slightly apical to the cervix of the root to prevent the growth in an apical dire ion of soft tissue along the root surface.

* * * * *